United States Patent [19]
Humke

[11] Patent Number: 4,673,665
[45] Date of Patent: Jun. 16, 1987

[54] PROCESS FOR TREATING ANESTRUS IN EWES OR BEEF CATTLE

[75] Inventor: Rainer Humke, Kelkheim, Fed. Rep. of Germany

[73] Assignee: Hoechst Aktiengesellschaft, Frankfurt am Main, Fed. Rep. of Germany

[21] Appl. No.: 456,253

[22] Filed: Jan. 6, 1983

[30] Foreign Application Priority Data

Jan. 9, 1982 [DE] Fed. Rep. of Germany ....... 3200459

[51] Int. Cl.$^4$ ...................... A61K 37/24; A61K 37/38
[52] U.S. Cl. ......................................... 514/15; 514/14; 514/800; 530/327; 530/328; 530/398; 530/399; 530/300
[58] Field of Search ............... 424/85, 88; 260/112 R; 424/177

[56] References Cited

PUBLICATIONS

McLeod et al, Proc. Ann. Conf. Soc. for the Study of Fert, Abstract No. 6, p. 13, Jul. 13–16, 1981.
Arendarcik et al, Endokronologie, vol. 76, No. 3, pp. 258–266 "Leutenizing Hormone . . . Gestagen Treatment".
Fujino et al., Chem. Abstr. 82, 51843c (1975).
Coy et al., J. Med. Chem. 19 (1976), pp. 423–425.
Schally et al., Vitamins and Hormones 38 (1980), pp. 257–323.
Sandow et al., Europ. J. Obstet. Gynaec. Reprod. Biol. 1976, 6/4, pp. 185–190.
Osland et al., Endocrin. 96(5), (1975), pp. 210–216.
Smith et al., J. Endocr. 48, 485–496 (1970).
Smith et al., J. Reprod. Fert. 55, 359–364 (1979).
Hauger et al., Endocrinology 101, 807–817 (1977).
Haresign et al., J. Reprod. Fert. 43, 269–279 (1975).
McNeilly et al., J. Reprod. Fert. 63, 137–144 (1981).
McLeod et al., Animal Breeding Abstracts 50, 598 (1982).
Austr. Vet. J. 60, 254–255 (1983).
McLeod et al., J. Reprod. Fert. 65, 223–230 (1982).

Primary Examiner—Thomas G. Wiseman
Assistant Examiner—Robin Lyn Teskin
Attorney, Agent, or Firm—Curtis, Morris & Safford

[57] ABSTRACT

A method for treating anestrus in ewes and beef cattle by treating a ewe or a beef cow for 4 to 16 days with a gestagen having protracted action, followed by administering LH-RH or an analogous compound of at least the same efficiency for 2 to 6 days to bring about an LH plasma level sufficient to induce ovulation.

3 Claims, No Drawings

PROCESS FOR TREATING ANESTRUS IN EWES OR BEEF CATTLE

Anestrus of beef cattle and ewes is characterized by a lack of rhythmic morphological changes in the female genital organs and by a lack of behavioral estrus. This state is caused by hormonal disturbances of the axis formed by the hypothalamus, the pituitary gland and the ovaries, as a consequence of which the ovarian activity has stopped.

Anestrus in beef cattle recurs in heifers to be mated or inseminated for the first time and in post-partum cows during a varying period of time. Post-partum anestrus in cows is particularly pronounced in the case of beef cows and dams nursing one or several calves. Owing to the fact that the efficiency of breeding a dam is determined by regular calving, if possible, at 1 year intervals, an animal breeder is greatly interested in keeping the anestrous period as short as possible.

The sheep is of a seasonal polyestrus nature, that means estrus recurs at regular intervals only during a defined season. The estrous period following conception and lambing starts with an anestrous phase of several months. The efficiency of sheep breeding could be distinctly increased if attempts would be successful to bring ewes artificially to estrus and to conception during this anestrous period, as a consequence whereof the annual reproduction rate would be practically doubled.

Attempts have been made for a long time to surmount anestrus in beef cattle and in ewes by administering various hormones, applied alone or in combination. In these tests, especially gestagens (progesterone and synthetic derivatives), partly in combination with estrogens and PMSG (pregnant mare's serum gonadotropin) in different forms of administration by way of injection, implantation and by oral or intravaginal application during a period of several days (for beef cattle cf. J. Anim. Sci., 19, 674–677 (1960); J. Anim. Sci., 25, 497–503 (1966); Tierärztl. Umschau, 26, 1–4 (1971); Vet. Rec., 101, 13–14 (1977); Vet. Rec., 104, 523–525 (1979); Vet. Reg., 104, 603–604 (1979); J. Reprod. Fert., 53, 289–296 (1978); J. Reprod. Fert., 54, 447–458 (1978); Theriogenology, 10, 307–312 (1978). Ewe: J. Endocrinol., 24, 33 (1962);1 J. Anim. Sci., 34, 1011–1019 (1972); Res. in Vet. Sci., 22, 324–329 (1977); J. Reprod. Fert., 44, 59–68 (1975); VIIIth Intern. Congr. Anim. Reprod, Krakow, 62 (1976); Theriogenology, 15, 389–403 (1981)).

Depending on various factors, especially on the breeds used and on the post-partum time of treatment, the results varied to a certain extent and the great majority thereof was unsatisfactory. The further search for improved methods capable of leading to better results while considering the natural hormonal regulation, was therefore understandable.

Some years ago it has been proved in various species that pulsed secretions of the luteinizing hormone (LH) produced in the pituitary gland and of the follicle stimulating hormone (FSH) occur prior to and during a menstrual cycle or estrous season, said secretions being apparently provoked by pulsed secretions of the LH/FSH-releasing hormone. Corresponding tests in beef cattle and in sheep are reported on by Yuthasastrakol et al. [J. Reprod. Fert., 50, 319–321, 1977) by Baird (Biology of Reproduction, 18, 359–364, 1978), by Carruthers et al. (J. Anim. Sci., 50, 919–925, 1980), by Forrest et al., (Biol. Reprod., 22, 197–201, 1980) and by Peters et al. (J. Reprod. Fert., 62, 567–573, 1981)]. A stimulation of these pulsed secretions of LH and FSH in non-cycling animals by a pulsed administration of LH-RH seemed therefore obvious. Corresponding tests in the sheep are described by McLeod and Haresign (Proc. Annual Conference Soc. for the Study of Fertility Abstr., 6, 15, 1980). Pulsed LH release following intravenous injections of 250, 500 and 1,000 ng, respectively, of LH-RH at 2 hourly intervals over a period of 8 days, could be measured and, depending on the dose applied, a LH surge similar to that occurring prior to ovulation, occured within a period of time of from 40 to 60 hours after the treatment. A rise in the progesterone level following ovulation could be observed during a period of from 10 to 12 days, said rise being accompanied by the development of a corpus luteum. Applying this method of treatment, estrus could not be induced, however, so that natural mating of the treated animals was not possible. It has been found moreover that said corpus luteum function did not correspond in most cases to that of a normal corpus luteum during a menstrual cycle.

Estrus and ovulation were induced only after a pretreatment of 5 sheep for 14 days by subcutaneously inserting an implant containing progesterone followed by an administration of 250 ng of LH-RH at 2 hourly intervals for 48 hours. 3 of 5 bred sheep became pregnant (cf. MeLeod and Haresign, Proc. Annual Conference Soc. for the Study of Fertility, Abstr., 6, 13, 1981).

Pulsed treatments using LH-RH at 1–2 hourly intervals were carried out as well in other species and resulted likewise in pulsed LH-release and in an onset of an ovarian cycle (cf. Humans: Crowley et al., J. Clin. Endocrinol. Metab., 51, 173–175, 1980; Leyendecker et al., 61st Ann. Endocrine Soc. Meeting, Anaheim, Calif., Abstr., 926, 1979; Beef cattle: Riley et al., 73rd Ann. Meeting Soc. Anim. Sci., North Carolina State University, Raleigh, Abstr. 1981; Monkey: Knobil, Rec. Progr. Horm. Research, 36, 53–88, 1980).

Attempts in the monkey to achieve the same pulsed LH release followed by induction of the menstrual cycle and ovulation by continuous intravenous injection of LH-RH failed, however (cf. Knobil. Rec. Progr. Horm. Research, 36, 53–88, 1980). It was to be expected therefore that a continuous administration of LH-RH in other species as well would not be capable of giving the same results as pulsed administration. On the other hand, a pulsed administration of active materials in agricultural livestock is expensive with regard to the time and costs involved and is therefore unacceptable for economic reasons.

It has now been found that an administration of a gestagen for 4 to 16 days to non-cycling sheep and beef cattle followed by continuous intravenous injection of about 250 ng of LH-RH/h over a period of from 2 to 6 days results in a pulsed LH release in the plasma, in an onset of estrus and in an induction of ovulation, which, after mating the animals, resulted in pregnancy.

The subject of the present invention therefore is a process for treating anestrus in ewes or beef cattle, which comprises treating a ewe or beef cattle for 4 to 15 days, preferably for 7 to 12 days, with a gestagen with protracted action and, upon complete treatment, bringing about a LH-plasma level sufficient for inducing ovulation by administering LH-RH or an analogous compound having at least the same efficiency for 2 to 6, preferably for 2 to 3, days. The dose of the gestagen with protracted action is chosen such that a blood plasma level of LH is induced during the time of treatment sufficient to inhibit LH and FSH release from the pituitary gland (cf. for example Endocrinology 108 (1981) 568–572, J. Reprod. Fert. 60 (1980) 177–185 and Res. Vet. Sci 22 (1977) 324–329).

Instead of LH-RH, analogous compounds that provoke a release of LH and FSH may alternatively be used for the purpose of the invention. Compounds distinguished by a rather strong biological action and by a protracted period of action are especially appropriate. Examples hereof are, in particular, analogous compounds having a D-amino acid in the 6-position, N-methyl leucine in the 7-position, and/or ethylamine, cyclopropylamine, or semicarbazide in the 10-position.

Suitable D-amino acids are, in particular, lipophilic amino acids, specifically D-Leu, D-Trp, D-Phe, D-ser(-Bu$^t$), D-His(Bzl), D-naphthylalanine, D-Glu(OBU$^t$) and D-Ada(OBu$^t$).

The LH-plasma level reached by administration of LH-RH and said LH-RH analogous compounds over said period of time can be maintained by using techniques and forms of administration with protracted action. Possible methods of administration include infusions, injections, transdermal applications or applications to mucous membranes, for example in the nose, having the known release characteristics, or implantable pharmaceutical forms such as depot bodies or pumps, intravaginal or intrauterine release systems or nose clips. Transdermal application or application to the mucous membranes requires a dosage 10 to 50 times higher, as experience has shown.

The gestagen treatment for 4 to 16 days applied in the first phase of the process of the invention may be done alternatively by using an implant as well as by using said administration techniques and said pharmaceutical forms characterized by a protacted gestagen release.

The ewe of generally 40–75 kg body weight may be pretreated with gestagen, for example by daily parenteral injection of from 5 to 25 mg, preferably of about 10 mg, of progesterone. A further possibility consists in subcutaneously inserting implants [for example Sil-Estrus ® of the firm Abbott or the implants described in J. Reprod. Fert. 60, (1980) 177–185] having a content of from 100 to 500 mg of progesterone for a period of from 6 to 14 days. Norgestomet ear implants (manufactured by the firm Searle) contain about 3 mg of norgestomet and are likewise inserted for a period up to 14 days. In intravaginal application, sponges containing from 10 to 50 mg, preferably of from 20 to 40 mg, of flurogestone acetate are preferably used, which are applied for a period of up to 14 days (for example Syncro-Mate ® sponges containing cronolone of the firm Searle). Oral treatment using MAP is described, by way of example, in J. Animal Sci., Albany, N.Y. 48 (1979) 1015–1019.

Beef cattle of 400 to 750 kg body weight in general may be pretreated with gestagen, for example by daily subcutaneous injection of from 20 to 200 mg, preferably of about 50 mg, of progesterone for a period of about 10 days. Alternatively, about 120 mg of dihydroprogesterone acetophenide daily may be given for about 10 days. The more efficient 10-nortestosterone is given orally in daily doses as low as bout 10 mg. Chlormadinone acetate is administered in equal doses as said hormones (cf. Berl. Münch. Tierärztl. Wschr. 86 [1973] 384–387). Synchro-Mate ® ear implants contain about 6 mg of norgestomet and remain in the animal up to 9 days. The intravaginal devices PRID ® (manufactured by the firm Abbott) contain up to 1.6 g of progesterone and remain in the body for 7 to 9 days.

The LH-RH treatment can be carried out in the following manner:

The doses of LH-RH or analogous compounds thereof, when administered to the ewe, are generally of from 20 to 1,000, preferably of from 50 to 500 ng/h (in intravenous application or infusion). Depot bodies implanted subcutaneously contain up to 500 μg, preferably from 10 to 100 μg, of LH-RH or the corresponding quantity of an analogous compound thereof (depot time of from 2 to 6 days).

Generally, from 40 to 2,000, preferably of from 120 to 1,000, ng of LH-RH/h (or the corresponding quantity of an analogous compound thereof) are administered to beef cattle intravenously or by infusion. Depot bodies implanted subcutaneously contain up to 6,000 μg, preferably of from 150 to 1,200 μg, of LH-RH or the corresponding quantity of an analogous compound thereof (depot time of from 2 to 6 days).

The following examples serve to illustrate the invention:

EXAMPLE 1

Implants containing progesterone were administered subcutaneously to 28 female mature ewes of two different breeds ("Clun Forest" and "Welsh Halfbred") for a period of 14 days.

12 Ewes were infused constantly with 125 to 250 ng of LH-RH per hour over a period of 48 hours 2 hours before withdrawing the implants. Four ewes treated with a saline solution served as a control. The sheep were examined by laparoscopy to test them for ovulation, moreover blood samples were taken to determine the progesterone level.

24 hours after starting the infusions, onset of estrus was observed using fertile rams at 4 hourly intervals and the ewes in estrus were mated.

The results are summarized in the following table:

| treatment | number of mated sheep | number of ovulations | rate of ovulations |
|---|---|---|---|
| 125 ng of LH-RH/h | 10* | 9** | 1.4 |
| 250 ng LH-RH/h | 11 | 12 | 1.5 |
| physiological saline solution | 0 | 0 | 0 |

*One ewe had lost the progesterone implant prior to the LH-RH treatment and could not be brought to estrus, consequently.
**One ewe could not be examined by laparoscopy because of internal adhesion.

Based on the progesterone data present at the time of filing of this patent application 9 to 12 ewes treated with LH-RH can be regarded as being pregnant.

The pregnancy rate of 75% achieved in this manner corresponds to the average value to be reached during a natural mating season.

EXAMPLE 2

17 Beef cows were injected with 1.0, 2.5 and 5.0 μg of LH-RH, respectively, in the early post-partum period during 2 to 4 days at 2 hourly intervals, while 21 beef cows were given a constant infusion of identical dosage per unit of time during the same period of time.

Blood samples were taken prior to and during the treatments to determine the LH level. Blood samples for determining the progesterone level were taken during a prolonged period of time after the treatment.

The results of the progesterone determination are summarized in the following table:

TABLE

| treatment | dose (μg) | number of cows total | No. showing progesterone rise |
|---|---|---|---|
| Injections at | 1.0 | 6 | 4 |
| 2 hourly intervals | 2.5 | 6 | 4 |
|  | 5.0 | 5 | 4 |
| Constant infusion | 1.0 | 6 + 3 | 2 |
| (μg/2 h) | 2.5 | 6 | 4 |
|  | 5.0 | 6 | 4 |

Following injections at 2 hourly intervals, a rise in the progesterone level indicating that ovulation had occurred was observed in 4 of 6 cows with 1.0 μg injections, in 4 of 6 cows with 2.5 μg injections and in 4 of 5 cows with 5 μg injections. Constant infusion in analogous doses resulted in a rise in the progesterone level in 2 of 9 cows, in 4 of 6 cows and in 4 of 6 cows.

6 of 9 cows to which a constant infusion of 1.0 μg/2 h had been given were treated after spring calvings and did not respond. The residual 3 cows have had calvings in summer, 2 animals responded.

A distinct increase in the plasma LH concentrations during the treatment phase, as compared to the pretreatment phase, was observed in all test animals, irrespective of the mode of administration and of said doses, the LH pulse frequency induced by the LH doses reflecting the endogenous LH release pattern observed during the control period.

It can be clearly deduced from said findings that a constant infusion of LH-RH to beef cattle results in the same pharmacological and clinical effects as pulsed administration of LH-RH.

EXAMPLE 3

5 Beef cows were treated in the early post-partum period over a period of 8 days by inserting in them an intravaginal device (PRID ® of the firm Abbott) containing progesterone. Following withdrawal of the device a LH-RH constant infusion in doses of 2.5 μg/2 h was carried out in the manner described in Example 2. Ovulation occurred during the treatment in all cows, said ovulation being characterized by an increase in the progesterone plasma level.

What is claimed is:

1. A method for treating anestrus in a ewe, heifer, or cow, which comprises treating the animal for 4 to 16 days with a gestagen and, following this treatment, continuously administering LH-RH or an analogous compound having at least the same efficiency intravenously, by infusion, or by implant for 2 to 6 days to bring about an LH plasma level sufficient to induce ovulation preceded by a fertile estrus and followed by normal luteal function.

2. A method for treating anestrus in a ewe, heifer, or cow, which comprises treating the animal for 4 to 16 days with a gestagen and, following this treatment, continuously administering LH-RH or an analogous compound having at least the same efficiency intravenously, by infusion, or by implant for 2 to 6 days to bring about an LH plasma level sufficient to induce ovulation preceded by a fertile estrus and followed by normal luteal function, said analogous compound having a D-amino acid in the 6-position, N-methyl-leucine in the 7-position, and/or ethylamine, cyclopropylamine, or semicarbazide in the 10-position.

3. A method as in claim 2 wherein said D-amino acid is selected from the group consisting of D-Leu, D-Trp, D-Ser(Bu$^t$), D-His(Bzl), D-naphthylalanine, D-Glu(OBu$^t$), and D-Aad(OBu$^t$).

* * * * *